Dec. 16, 1930. A. E. SMITH Re. 17,906

HYPODERMIC SYRINGE

Original Filed May 18, 1925

INVENTOR.
ARTHUR E. SMITH

BY B. J. Craig

ATTORNEY.

Reissued Dec. 16, 1930 Re. 17,906

UNITED STATES PATENT OFFICE

ARTHUR E. SMITH, OF LOS ANGELES, CALIFORNIA

HYPODERMIC SYRINGE

Original application filed May 18, 1925, Serial No. 31,029. Renewed September 23, 1926. Original No. 1,607,271, dated November 16, 1926. Application for reissue filed February 12, 1927. Serial No. 167,853.

This invention relates to hypodermic syringes and it has for its object to provide a device of this character into which a medicinal package of the nature of an ampule may be charged, after the manner of loading a gun, the several parts being so correlated and arranged that a freshly made medicinal preparation may be injected by the syringe without ever coming into contact with human hands, unsterilized receptacles or with the atmosphere.

It is a further object of the invention to provide a syringe of the character indicated adapted to form the necessary fluid tight joint between the ampules and the syringe, with facility and dispatch and with very little trouble upon the part of the user.

Further objects of the invention and refinements of construction will be pointed out in the detailed description which follows:

In the accompanying drawings.

Like numerals designate corresponding parts in all of the figures of the drawing.

Figure 6:
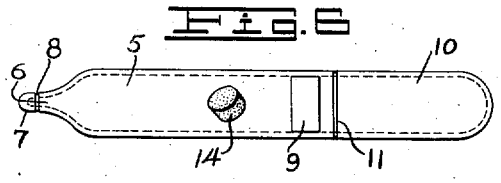
Fig. 6 is a side view of the ampule, hereinafter described.
Figure 2:
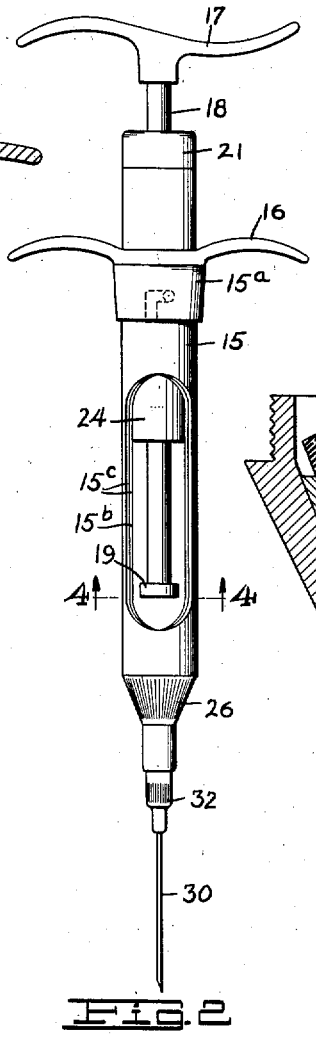
Fig. 2 is a side elevation of the syringe upon a smaller scale.
Figure 4:
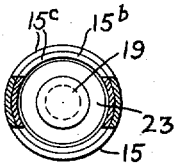
Fig. 4 is a transverse sectional view upon line 4—4 of Fig. 2.

The syringe of the present invention is particularly designed to discharge the contents of the ampule shown in Fig. 6. This ampule comprises a glass body 5, having a tapered front end 6, which terminates in a breakable tip 7. This tip is rendered readily separable from the remainder of the ampule by scoring, notching, etching, or otherwise weakening it as indicated at 8. The ampule contains a rubber or other stopper 9 which is adapted to act as a piston to expel the contents of the ampule through the open tapered end 6 of the ampule, after it has been broken therefrom, as hereinafter described. I preferably close the rear end of the ampule indicated at 10 and weaken it by a scored or cut line, at 11, so that this rear end may be readily broken therefrom. Thus this closed rear end protects the stopper and maintains the whole in absolutely sterile condition until the time of use arrives.

Certain medicinal compounds, and particularly certain anesthetics are unstable in solution, and this disintegration or chemical change may produce deleterious effects upon the patient if such a solution was injected. Such medicinal compounds should be freshly prepared at the time of use. In the present case the constituent elements of the medicinal preparation in the ampules, are maintained separate from the vehicle until the time of use arrives. For example, the body of liquid indicated at 12, in the ampule, may be distilled water, and an anesthetic or other medicinal preparation in the form of tablets or powder may be contained within a paraffin or other waterproof capsule 14, which is fusible or meltable under a comparatively low degree of heat. Thus when the time of use arrives, by placing the ampule into warm water and increasing the temperature or holding it under running hot water, the paraffin or low fusible wall may be melted and the medicinal ingredients permitted to mix with the distilled water or other vehicle. By holding the ampule in a vertical position with its large end upward, the released paraffin will travel upward, due to its specific gravity, and find a seating in the concave face $9^a$ of the stopper 9, so that it will thereafter constitute, in effect, a part of the piston in ejecting the medicinal preparation through the open end of the ampule. When the paraffin rises it is still hot and in molten condition. After it has entered and seated itself in the concave face of the stopper, it is congealed and hardened, in contact therewith, by placing the ampule in cold water or holding it with large end upward under running cold water.

The syringe comprises a barrel 15 having a bayonet joint connection with a head $15^a$, the latter carrying a cross bar 16, for engagement by the fingers of the operator, the palm of whose hand engages a handle or cross bar 17 upon the upper end of a plunger rod 18. This plunger rod carries a plunger 19 at its inner end which is adapted to engage the stopper 9 and force said stopper downwardly to expel the liquid 12 from the ampule. The plunger rod 18 is surrounded by a spring 20, the upper end of which bears against a cap 21 having a bayonet joint connection 22 with the head 15[a] and the lower end of which bears against the flange 23 of a sliding sleeve 24. Thus the sleeve and the flange constitute a yieldable pressure exerting element, adapted to bear upon the rear or upper end of the ampule along the broken off line 11, to thereby force the nose of the ampule into engagement with a suitable packing element, preliminary to the operation of handle 17.

Figure 3:
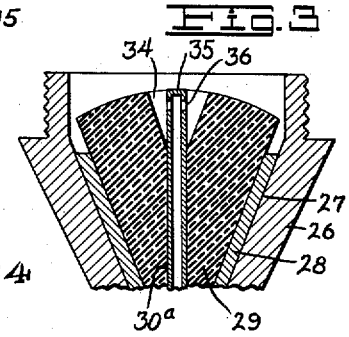
Fig. 3 is a magnified sectional view of the lower portion of the syringe, illustrating an elastic packing cone, and a discharge tube hereinafter described.
Figure 5:
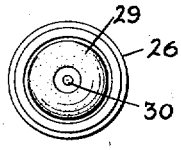
Fig. 5 is a plan view of the structure illustrated in Fig. 3, upon a smaller scale.

The barrel 15 is internally threaded at 25 for the reception of a head 26. This head is provided with a conical chamber 27 and this chamber in turn receives a thin metal funnel 28, which constitutes a seating for a conical rubber packing element 29. The hypodermic needle 30 is provided with an enlarged portion 31 which lies between the lower end of the metallic cones 28 and a tip 32, the latter being threaded at 33 into engagement with the lower end of the head 26. The upper end of the enlarged portion 31 of the needle bears against and is seated in the concave bottom of the metallic funnel 28. The rubber cone 29 is provided with a convex upper face and has a central tapering depressison formed in said upper face which receives the lower end of the ampule after the tip has been broken off. The upper portion of the needle, indicated at 30[a], passes through the rubber cone, and extends upwardly through the conical recess 34 of the cone. The upper end of the needle is preferably closed, as indicated at 35 in Figure 3 and it is provided with a plurality of lateral openings 36 to permit the passage of liquid from the ampule to the interior of the needle. The closing of the upper end of the needle in the manner described, is to obviate the possibility of the needle becoming accidentally clogged by the paraffin.

When the head 26 is screwed into place it compresses the rubber cone 29 against a ring 37, which is secured in the lower end of the barrel 15 and which is provided with a beveled face 38. The conical shape of the recess 27 in conjunction with the pressure exerted by the ring 37 causes an inward compression of the cone 29 about the portion 30[a] of the needle, while the forcing of the broken tapered end of the ampule into the recess 34 of the cone 29 brings about an outward compression of the upper portion of said cone. Thus a fluid tight joint is provided between the cone and the needle, between the ampule and the cone and between the cone and the ring 37, which absolutely insures against any leakage of the contents of the ampule. The head 15[a] carries an elongated sleeve 15[b], which is adapted to slide downwardly within the barrel 15, and the sleeve 15[b] and barrel 15 are provided with sight openings 15[c] through which the contents of the ampule and the movement of the plunger and stopper 9 may be viewed. Furthermore, the presence of these openings facilitates the proper engagement of the nose of the ampule with the openings 34 of the cone 29.

One of the most important features of the present invention is the provision of the yielding sleeve 24. This construction renders it possible to handle ampules of varying sizes and consequently of varying cubic capacities.

The syringes that I have manufactured up to the present time are adapted to handle ampules ranging from one to four cubic centimeters in capacity, or any fractions thereof, and it is clear from the construction illustrated and described that the yielding sleeve 24 will serve to preliminarily establish a fluid tight joint between the needle and the ampule, irrespective of the length of the ampule (within certain limits) and thus render it possible for the physician or surgeon to use a single syringe, to handle a number of varying sizes of ampules.

While I have stated that I preliminarily weaken the ampule at the points to be broken off, it is to be understood that this is not absolutely essential, since the physician may accomplish this result by suitably nicking or notching the ampule with a small file, at the time of use.

Figure 1:
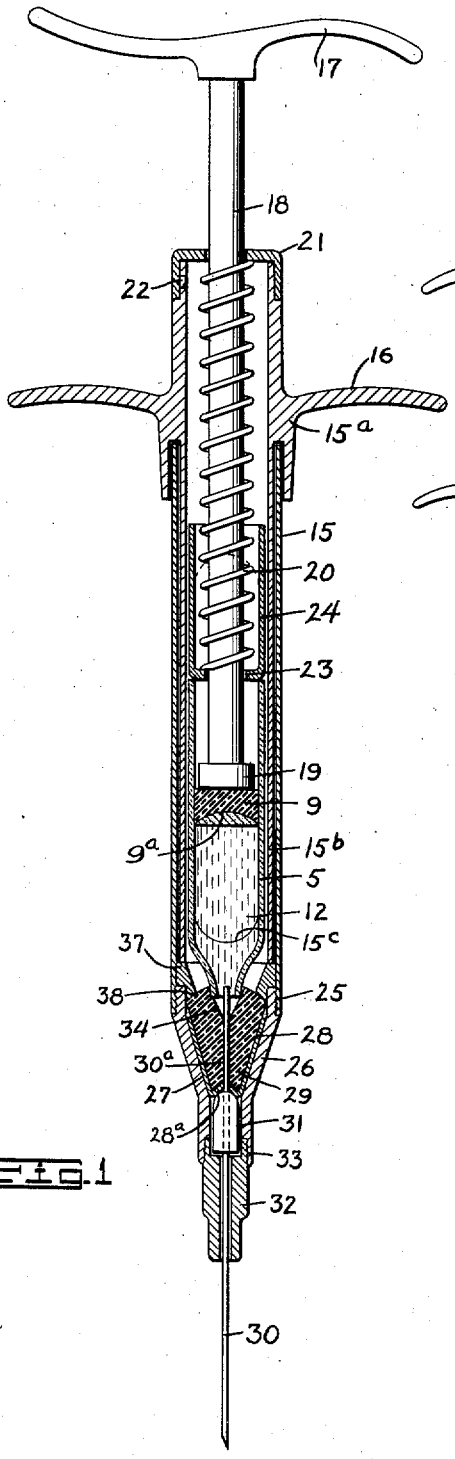
Fig. 1 is an enlarged vertical sectional view of a syringe constructed in accordance with the invention.

It is thought that the operation of this device will be apparent without further description. However, it may briefly be stated that in use, the operator separates the barrel 15, from sleeve 15[b], by disengaging the bayonet connections. He then selects the proper size ampule and after heating and cooling it as previously described, breaks off the tip, and the rear end. and places this ampule in the barrel 15 with its broken off, smaller end, seated in the recess 34. The parts are magnified above normal in Figure 1 and the opening that is left in the end of the ampule after its tip is broken off is so small that the liquid does not run out of this opening until pressure is applied thereto by the forcing of the cork downwardly into the ampule. After the ampule has been seated in contact with the cone 29, as described, the sleeve 15[b] is slipped downwardly within the barrel 15 and about the ampule and the bayonet connection of head 15[a] is made, to join said head and sleeve. This brings the sleeve 24 and its flange 23 to bear with yielding pressure upon the upper end of the ampule, and forces the nose of the ampule into contact with the cone 29. When pressure is applied to the handle 17 to force the plunger downwardly, said plunger contacts with the stopper 9 and exerts pressure upon the liquid within the ampule. This pressure upon the liquid in turn tends to force the ampule downwardly and increases the pressure upon the packing cone 29 and associated parts.

It is to be noted that the funnel 28 has a concave bottom 28[a]. This facilitates the entry of the needle through the cone 29, the lower end of the cone conforming in shape to the lower end of the funnel.

It is to be understood that the invention is not limited to the precise construction set forth but that it includes within its purview whatever changes fairly come within either the terms or the spirit of the appended claims.

Having thus described my invention, what I claim is:

1. A syringe of the character described comprising a barrel having a compressible packing element at the lower end thereof adapted to make fluid tight contact with an ampule, a sleeve adapted to have sliding engagement with said barrel, a detachable connection between the sleeve and the barrel, a plunger and plunger rod operating in the sleeve and a yielding pressure member surrounding the plunger rod and longitudinally movable within said sleeve.

2. A syringe of the character described comprising a barrel having a compressible packing element at the lower end thereof adapted to make fluid tight contact with the small broken end of an ampule, a sleeve adapted to have sliding engagement with said barrel, a detachable connection between the sleeve and the barrel, a plunger and plunger rod operating in the sleeve, a pressure member surrounding the plunger rod and longitudinally movable within said sleeve, a cap upon the sleeve and a spring bearing between said cap and said pressure member.

3. In a device of the character described, the combination with a barrel, of a compressible packing member at the lower end thereof adapted to make contact with an end of an ampule, a cap within which said packing member is seated, a removable tip for said cap and a hypodermic needle having an enlarged portion lying inwardly of said tip, and compressed by said tip against the packing member, there being a portion of said needle above said enlarged portion which projects through the packing element.

4. In a device of the character described, the combination with a barrel, of a cap threaded into the lower end thereof and having a conical recess formed therein, a thin metallic funnel-like member seated in said recess, a compressible packing element in said funnel, a removable tip threaded into the cap and a hypodermic needle having an enlarged portion intermediate its ends and through which the outer portion of the needle passes, said tip engaging the enlarged portion of the needle and forcing it against the lower end of the funnel-like member.

5. A structure as recited in claim 4 wherein said funnel-like member is provided with a concave lower end within which the enlarged portion of the needle has a seating.

6. A structure as recited in claim 4 wherein the lower portion of the funnel-like member has a concave recess formed therein within which the enlarged member of the needle has a seating, that portion of the needle above the enlarged portion projecting through the compressible packing element and terminating slightly above the upper surface thereof.

7. A structure as recited in claim 4 wherein said needle has a closed upper end and lateral openings below said upper end.

8. A syringe of the character described, comprising a barrel having an internally threaded lower end, a head threaded into engagement therewith, a ring within the barrel adjacent its lower end, a packing element having a convex upper face and conically recessed lower and upper end portions, seated in said head, a tip threaded into the lower end of said head, a hypodermic needle having an enlarged portion forced against the concave lower face of the packing element by said tip when the latter is screwed into position, said packing element being forced into engagement with said ring when the head is screwed into position and said needle comprising a portion above said enlarged portion thereof which projects upwardly through the packing element and terminates slightly above the upper face of the said packing element.

9. A syringe of the character described, comprising a barrel, a sleeve slidable in said barrel, a spring actuated pressure element movable in said sleeve, a ring in the barrel adjacent the lower end thereof having a beveled lower face, a cap having screw threaded engagement with the lower end of the barrel, a tip having threaded engagement with the lower end of the cap, said cap having a conical interior, a metallic funnel-like element seated in said cap, a conical rubber packing element seated in said funnel-like member having a concave lower face, said packing element having a conical recess formed in its upper face, a hypodermic needle having an enlarged portion which lies between the tip and the lower end of the funnel-like element, the outer portion of said needle projecting through the packing element and into the conical recess formed in the upper face thereof.

10. A syringe adapted to receive an ampule and having means at its discharge end to make fluid tight connection directly with the forward end of the body of an ampule, a plunger adapted to operate in said ampule, and means on the interior of the syringe coacting with said ampule and adapted to hold the ampule in place in the syringe independently of the thrust of the plunger.

11. The combination of a syringe including a barrel having an apertured compressible member at one end, and an ampule having a neck portion apertured and engaging said compressible member, said ampule having a cylindrical inner wall, a plunger movable in the wall, the ampule having a smooth end and a member movable in the barrel adapted to engage the end and hold the ampule in place and means extending into the barrel for moving said plunger.

12. A syringe adapted to receive an ampule, and having means at its discharge end to make fluid tight connection directly with the forward end of the body of the ampule, a plunger adapted to operate in said ampule and a resilient pressure exerting means adapted to bear against the rear end of the ampule and to force the ampule bodily toward the discharge end of the syringe independently of the thrust of the plunger.

13. A hypodermic syringe comprising an ampule having a pointed front end and a stopper for its rear end, front, rear and intermediate members, the rear member being separable from the intermediate member to permit the introduction and removal of the ampule, and a longitudinally yielding inner member carried by the syringe rear member for engaging the rear end of the ampule to press it forwardly.

14. A hypodermic syringe comprising an ampule having a pointed front end and a stopper for its rear end, front, rear and intermediate members, the rear member being separable from the intermediate member to permit the introduction and removal of the ampule, a longitudinally yielding inner member carried by the syringe rear member for engaging the rear end of the ampule to press it forwardly, and a tapered washer in the front member forming a yielding cushion for the pointed front end of the ampule.

15. A hypodermic syringe comprising an ampule having a pointed front end and a stopper for its rear end, front, rear and intermediate members, the rear member being separable from the intermediate member to permit the introduction and removal of the ampule, a longitudinally yielding inner member carried by the syringe rear member for engaging the rear end of the ampule to press it forwardly, a tapered washer in the front member forming a yielding cushion for the pointed front end of the ampule, and a plunger slidable in the inner member having its head positioned to force the ampule stopper along within the ampule to eject the contents thereof.

16. The combination of a hypodermic syringe comprising a body including front, rear and intermediate body members and an ampule in said body, said ampule having a tapered end, said rear member being separable from the intermediate member to permit the introduction and removal of the ampule, yielding means carried by the body for engaging the ampule to hold it in position, a washer positioned in the front member and forming a packing between said tapered end and the front member, a stopper in the ampule and means to move the stopper within the ampule to eject the contents thereof.

17. A syringe adapted to receive an ampule, and having means at its discharge end to make fluid tight connection directly with the forward end of the body of an ampule, a plunger adapted to operate in said ampule and a yieldable telescopic pressure exerting means adapted to bear against the rear end of the ampule.

18. A syringe adapted to receive an ampule, and having means at its discharge end to make fluid tight connection directly with the forward end of the body of an ampule, a plunger adapted to operate in said ampule, a telescopic element adapted to bear against the rear end of the ampule and a spring disposed in said telescopic element for forcing it against said ampule.

19. A syringe of the character described comprising a tip having a conical recess therein, a conical elastic element seated in said recess and a discharge tube extending through said conical elastic element, said elastic element being provided with a conical recess adapted to receive the small broken end of an ampule, the upper end of the discharge tube projecting above the lower end of said recess.

20. A syringe of the character described comprising a tip having a conical recess therein, a conical elastic element seated in said recess and a discharge tube, said elastic element having a conical recess in its upper face and wherein the discharge tube extends through said element and projects above the bottom of said conical recess and has a closed upper end with lateral openings therein below said closed upper end.

21. In a syringe of the character described, the combination with a barrel, of a cap adapted to be screwed into engagement therewith, a ring carried by the lower end of the barrel having a beveled lower face, a conical recess in the cap, a conical rubber cone seated in said recess and a discharge tube extending upwardly through said cone.

22. A structure as recited in claim 21 wherein said cone is provided with a tapering recess in its upper face.

23. A structure as recited in claim 21 wherein said rubber cone is provided with a convex upper face and a conical downwardly tapering recess, centrally formed in its upper face.

24. A structure as recited in claim 21 wherein said rubber cone is provided with a central tapering recess formed in its upper face, and wherein said discharge tube projects above the bottom of said recess.

25. A structure as recited in claim 21 wherein said cone is provided with a central tapering recess and wherein said discharge tube projects above said recess and is provided with a closed upper end and lateral openings below said closed upper end.

26. A syringe adapted to receive an ampule having a tapered discharge end and having means at its discharge end to make fluid tight connection with the forward end of the body part of an ampule, a plunger adapted to operate in said ampule and a resilient pressure exerting means adapted to bear against the rear end of the ampule and to force the ampule bodily toward the discharge end of the syringe independently of the thrust of the plunger, said first mentioned means comprising an elastic element engaging said tapered end whereby a conical fluid tight seal is provided.

27. A syringe of the character described, comprising a barrel, an ampule engaging member movable within said barrel, a plunger element movable through said ampule engaging member in said barrel, said barrel having an interiorly tapered lower end portion, a rubber packing element fitted in said tapered portion, said packing element being flared at its upper end and having an aperture therethrough, and an ampule in said barrel, said ampule having a tapered lower end fitting the flared portion of said packing element.

28. A syringe of the character described, comprising a barrel, an ampule engaging member movable within said barrel, a plunger element movable through said ampule engaging member in said barrel, said barrel having a cylindrical lower end, said barrel including an apertured closure for the cylindrical lower end, said closure having a tapered interior, a rubber packing element fitting in said tapered interior, said packing element having an aperture therethrough, the upper end of the aperture being flared, an ampule in said barrel, said ampule having a tapered end fitting in the flared portion of said packing element aperture and a hypodermic needle on said barrel.

In testimony whereof, I hereunto affix my signature.

ARTHUR E. SMITH.